(12) United States Patent
Petyaev et al.

(10) Patent No.: US 9,547,001 B2
(45) Date of Patent: Jan. 17, 2017

(54) ANTIBODY SPECIFIC FOR TRANS-RESVERATROL AND USE THEREOF

(71) Applicant: IP Science Limited, Cambridge (GB)

(72) Inventors: Ivan Petyaev, Cambridge (GB); Valery Tsybezov, Moscow (RU)

(73) Assignee: IP Science Limited, Cambridge (GB)

( * ) Notice: Subject to any disclaimer, the term of this patent is extended or adjusted under 35 U.S.C. 154(b) by 0 days.

(21) Appl. No.: 14/357,729

(22) PCT Filed: Nov. 9, 2012

(86) PCT No.: PCT/GB2012/052790
§ 371 (c)(1),
(2) Date: May 12, 2014

(87) PCT Pub. No.: WO2013/068758
PCT Pub. Date: May 16, 2013

(65) Prior Publication Data
US 2014/0349319 A1  Nov. 27, 2014

(30) Foreign Application Priority Data
Nov. 11, 2011 (GB) .................................. 1119585.6

(51) Int. Cl.
| | | |
|---|---|---|
| C07K 16/44 | (2006.01) |
| G01N 33/53 | (2006.01) |
| C07K 16/14 | (2006.01) |
| G01N 33/74 | (2006.01) |
| G01N 33/94 | (2006.01) |
| A61K 39/395 | (2006.01) |

(52) U.S. Cl.
CPC ........... *G01N 33/5308* (2013.01); *C07K 16/14* (2013.01); *C07K 16/44* (2013.01); *G01N 33/74* (2013.01); *G01N 33/94* (2013.01); *A61K 39/39583* (2013.01); *C07K 2317/30* (2013.01); *G01N 2430/00* (2013.01)

(58) Field of Classification Search
CPC ........................... C07K 16/44; G01N 33/5308
See application file for complete search history.

(56) References Cited

FOREIGN PATENT DOCUMENTS

| RU | 2385457 C1 | 3/2010 |
| WO | WO-2006125000 A2 | 11/2006 |

OTHER PUBLICATIONS

Hain et al, "Expression of a stilbene synthase gene in Nicotiana tabacum results in syntheis of the phytoalexin resveratrol", Plant Molecular Biology, vol. 15, pp. 325-335, published 1990.*
Chappey et al, "Monoclonal Antibodies in Hapten Immunoassays", *Pharmaceutical Research*, vol. 9, No. 11, 1992, pp. 1375-1379.
(Continued)

*Primary Examiner* — Shafiqul Haq
*Assistant Examiner* — Nam Nguyen
(74) *Attorney, Agent, or Firm* — Norton Rose Fulbright US LLP

(57) ABSTRACT

The present invention provides a method of detecting or measuring trans-Resveratrol (tRV) in a sample, comprising: contacting a sample to be tested with an antibody against tRV, or an antigen binding fragment of such an antibody; and detecting or measuring any tRV bound by the antibody or antibody fragment. The invention also provides an antibody against trans-Resveratrol.

11 Claims, 11 Drawing Sheets

(56) References Cited

OTHER PUBLICATIONS

Chu et al, "Direct Analysis of Resveratrol in Wine by Micellar Electrokinetic Capillary Electrophoresis", *Journal of Agricultural and Food Chemistry*, vol. 46, No. 2, 1998, pp. 509-513.

He et al, "High-performance liquid chromatography spectrometric analysis of trans-resveratrol in rat plasma", *Journal of Chromatography B: Biomedical Sciences & Applications*, No. 832, 2006, pp. 177-180.

Moesta et al, "Development of a Radioimmunoassay for the Soybean Phytoalexin Glyceollin $I^1$", *Plant Physiology*, No. 73, 1993, pp. 233-237.

Nemcova et al, "Determination of resveratrol in grains, hulls and leaves common and tartary buckwheat by HPLC with electrochemical detection at carbon paste electrode", *Food Chemistry*, No. 126, 2011, 374-378.

Paulo et al, "Development and Validation of an Analytical Method for the Determination of trans- and cis-Resveratrol in Wine: Analysis of its Contents in 186 Portuguese Red Wines", *Journal of Agricultural and Food Chemistry*, No. 59, 2011, pp. 2157-2168.

Petyaev et al, "Generation of Monoclonal Antibody Against trans-Resveratrol", *Hybridoma*, vol. 31, No. 6, 2012, pp. 1-6.

Wang et al, "Molecular imprinted polymer-based chemiluminescence imaging sensor for the detection of trans-resveratrol", *Analytica Chimica Acta*, No. 592, 2007, pp. 115-120.

Yau et al, "Emerging trends in the synthesis and improvement of hapten-specific recombinant antibodies", *Biotechnology Advances*, No. 21, 2003, pp. 599-637.

Zhang et al, "Review on enzyme-linked immunosorbent assays for sulphonamide residues in edible animal products", *Journal of Immunological Methods*, No. 350, 2009, pp. 1-13.

Paulo, Luisa; et al, Development and Validation of an Analytical Methods of the Determination of trans- and cis-Resveratrol in Wine: Analysis of its Contents in 186 Portuguese Red Wines; Journal of Agricultural and Food Chemistry; 2011, 59, 2157-2168.

\* cited by examiner

ANTIBODY SPECIFIC FOR TRANS-RESVERATROL AND USE THEREOF

CROSS REFERENCE TO RELATED APPLICATIONS

This application is a national phase application under 35 U.S.C. §371 that claims priority to PCT Application No. PCT/GB2012/052790 filed on Nov. 9, 2012, which claims the benefit of Great Britain Application No. 1119585.6 filed Nov. 11, 2011, all of which are incorporated herein by reference in their entireties.

FIELD OF THE INVENTION

The present invention relates to antibodies against trans-Resveratrol, as well as assays for trans-Resveratrol employing such antibodies.

BACKGROUND TO THE INVENTION

There is substantial interest in trans-Resveratrol (tRV). It is thought that the health benefits of drinking red wine may largely be due to the presence of trans-Resveratrol. Such benefits include the lower rate of cardiovascular heart disease (CVD) associated with the consumption of red wine. Research is also ongoing into potential anti-aging, anti-cancer and anti-diabetic effects of trans-Resveratrol. Given those potential benefits, the production of foods, beverages and food supplements with high trans-Resveratrol levels is highly desirable.

Despite the high level of interest in trans-Resveratrol and its effects from the wine-making and pharma industries, reflected in the thousand of publications related to trans-Resveratrol, the only method for measuring trans-Resveratrol to date is High Performance Liquid Chromatography Mass Spectroscopy (HPLC-MS). Although HPLC-MS is a specific and sensitive assay method it has significant limitations, primarily due to the cost of equipment for performing HPLC-MS and low through-put rates. For instance, despite the fact that wine makers want to be able to assess levels of trans-Resveratrol at individual stages of wine production, and also to produce vines giving high levels of trans-Resveratrol, there are only a handful of HPLC-MS facilities in France, meaning analysis is costly and slow, making it difficult to analyse trans-Resveratrol levels over time.

SUMMARY OF THE INVENTION

The present invention provides a much faster and cheaper way to detect and measure tRV. The method provided is an antibody based approach for such detection. In particular, the present invention provides a method of detecting or measuring trans-Resveratrol (tRV) in a sample, comprising:
 (i) contacting a sample to be tested with an antibody against tRV, or an antigen binding fragment of such an antibody; and
 (ii) detecting or measuring any tRV bound by the antibody or antibody fragment.

The present invention further provides:
 an antibody against tRV, or an antigen binding fragment of such an antibody;
 a hybridoma selected from the hybridoma deposited under Accession Number VKPM H-121, the hybridoma deposited under Accession Number VKPM H-122 and a hybridoma producing the same antibody as those deposited under Accession Numbers VKPM H-121 and VKPM H-122; and
 a kit for detecting or measuring trans-Resveratrol (tRV), where the kit comprises such an antibody or antibody fragment.

DETAILED DESCRIPTION OF THE INVENTION

Figure 1:
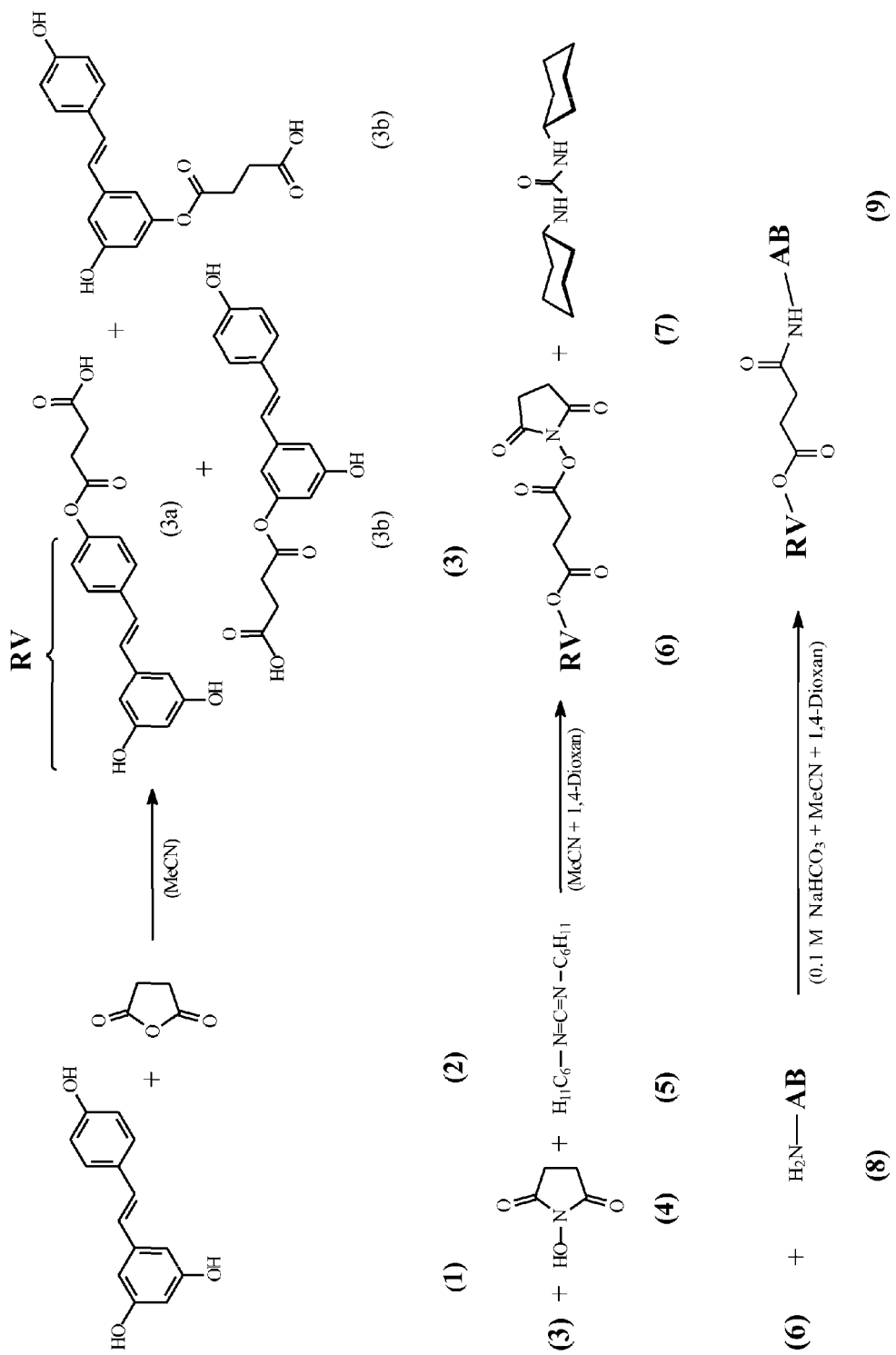
FIG. 1 shows the synthesis of the tRV conjugate used in generating anti-tRV antibodies.
Figure 2:
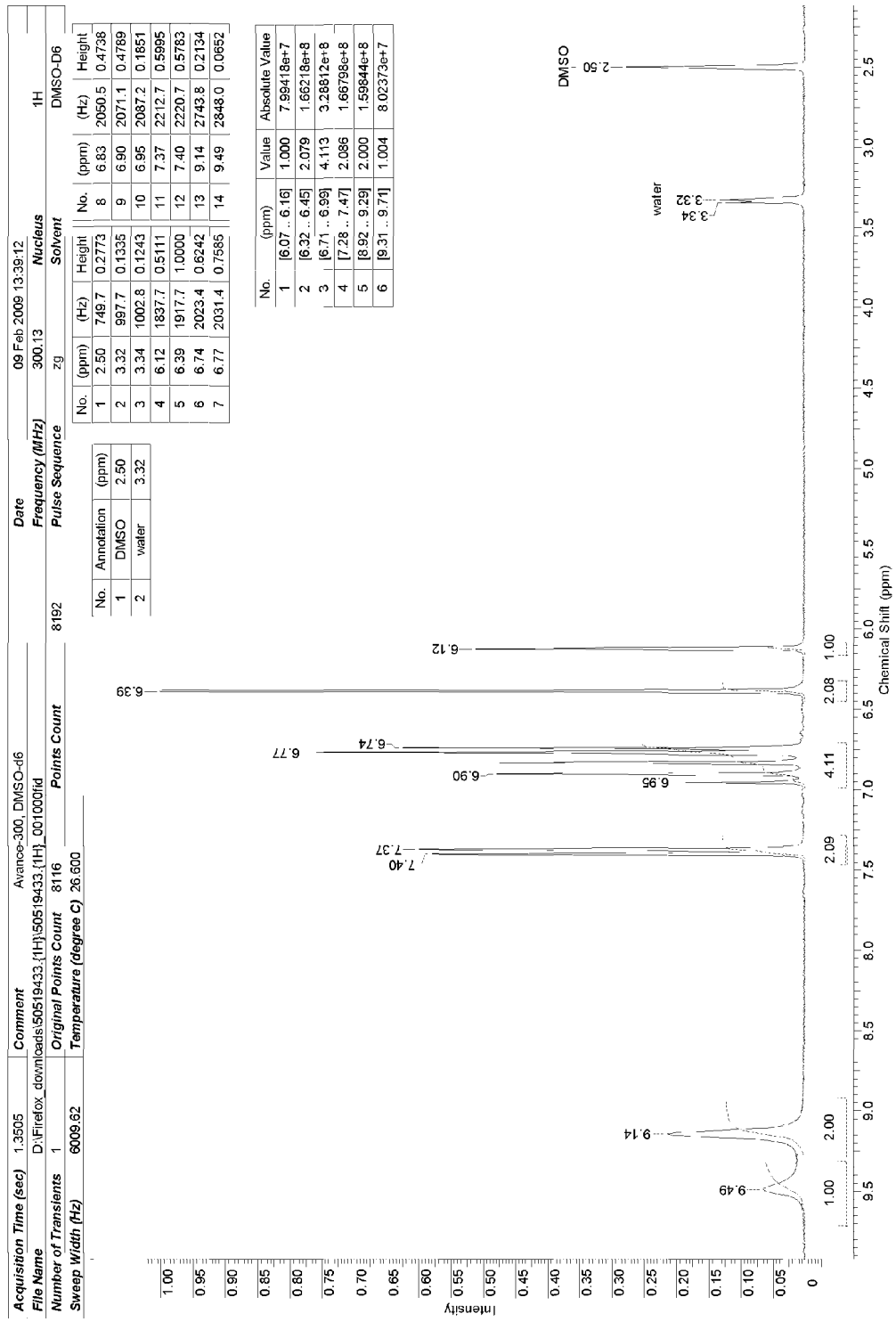
FIG. 2 shows $^1$H-NMR spectrum of tRV in DMSO-$d_6$ at 300 MHz, Bruker AM300.

It is to be understood that different applications of the disclosed methods may be tailored to the specific needs in the art. It is also to be understood that the terminology used herein is for the purpose of describing particular embodiments of the invention only, and is not intended to be limiting. In addition as used in this specification and the appended claims, the singular forms "a", "an", and "the" include plural referents unless the content clearly dictates otherwise. Thus, for example, reference to "a compound" includes "compounds", reference to "a polypeptide" includes two or more such polypeptides, and the like. All publications, patents and patent applications cited herein, whether supra or infra, are hereby incorporated by reference in their entirety. Where the term "comprising" is used herein, the invention also provides embodiments "consisting of" and "consisting essentially of" the specified constituents.

The present invention is based on the provision by the inventors of antibodies against trans-Resveratrol (tRV), particularly monoclonal antibodies against tRV. The invention also provides an assay for trans-Resveratrol employing such antibodies. The antibody based assays provided are more cost-effective, faster and significantly more affordable than the conventionally employed High Performance Liquid Chromatography Mass Spectroscopy (HPLC-MS). Preferably the assay of the invention is an ELISA, though the antibodies may be used in other antibody based assay formats.

Surprisingly antibody based assays have not previously been developed to measure trans-Resveratrol and it is thought that this may be due to a number of technical difficulties in providing such antibodies, in particular difficulty in obtaining: (i) an effective immunogenic complex of not-immunogenic per se hapten with trans-Resveratrol with an immunogenic matrix; and (ii) significantly active mouse trans-Resveratrol-producing hybridomas with sufficient stability of its clones. Molecules of trans-Resveratrol have an amphiphilic, even more hydrophobic than hydrophilic, properties and ability to form clusters with each other and other suitable structures, affecting exposure of immunogenic epitopes. Despite such technical difficulties, the inventors have successfully raised monoclonal antibodies against trans-Resveratrol, further resulting in the production of effect assays for trans-Resveratrol.

In addition, the present inventors have also unexpectedly found that the overall concentrations of trans-Resveratrol in serum measured by ELISA were significantly higher than those measured by HPLC-MS (Table 1a, b). This difference between the results obtained using the conventional assay and the antibody based assays of the invention may be the result of the different ways samples are prepared for HPLC-MS analysis and antibody-based assays. For HPLC-MS protein fractions must be precipitated and removed from the serum prior to analysis, whereas antibody based assays, particularly ELISA, do not require such precipitation. Hence, in HPLC-MS protein-associated or bound tRV, if present in the sample, may be removed in the precipitation step and so not be measured, or even detected, whereas such tRV will be measured in antibody based assays. Hence, the assays of the invention may be more accurate in detection and measurement of tRV, because they allow for detection of all the tRV in a sample, without loss due to precipitation. Hence, sample preparation for the assays of the invention will typically lack a precipitation step.

A further advantage of the assays of the invention is that they allow detection of a completely new pool of tRV in the blood, and other types of analytical samples, which is associated with lipoproteins. For example, the use of HPLC-MS for analysis of serum from volunteers for the presence of tRV completely failed to detect such molecules at any level in their serum. At the same time by using the assays of the invention it was possible to measure a significant level of tRV in the same samples (see Table 3 below). Hence, the antibody based assays of the invention may provide more representative results than HPLC-MS, because of their ability to detect such tRV and further may be particularly effective for analysing biological samples, particularly blood, plasma and serum, and preferably plasma.

The provision of the antibody based tests of the invention means detection of tRV is far more affordable and also gives an antibody-based "tRV-Scale" for wine and other beverages, or even food, contacting trans-Resveratrol. Such a scale could not have been provided via the conventional HPLC-MS measurement. The fact that the antibody based assays of the invention are relatively cheap and easily performed means that individual food and beverage producers are able to perform the assays themselves, obtaining the results quickly, not needing to rely on expensive HPLC-MS based analysis only available at a limited number of sites and taking time to obtain the results from.

Antibodies

The present invention provides antibodies against tRV. In particular, the invention provides monoclonal antibodies against tRV.

The term "antibody" as referred to herein includes whole antibodies and any antigen binding fragment (i.e., "antigen-binding portion") or single chains thereof. An antibody refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. Each light chain is comprised of a light chain variable region (abbreviated herein as $V_L$) and a light chain constant region. The variable regions of the heavy and light chains contain a binding domain that interacts with an antigen. The $V_H$ and $V_L$ regions can be further subdivided into regions of hypervariability, termed complementarity determining regions (CDR), interspersed with regions that are more conserved, termed framework regions (FR).

Antibodies of the invention may be monoclonal or polyclonal. In particular, either monoclonal antibodies or polyclonal antisera may be used. Particularly preferred are monoclonal antibodies. A monoclonal antibody of the invention may be a chimeric antibody, a CDR-grafted antibody, a single-domain antibody, a human or humanised antibody or an antigen-binding portion of any thereof. For the production of monoclonal antibodies, the experimental animal is typically a non-human mammal such as a goat, rabbit, rat or mouse but antibodies may also be raised in other species such as camelids. In one preferred instance, the monoclonal antibody of the invention is a murine monoclonal antibody.

Monoclonal antibodies (mAbs) of the invention can be produced by a variety of techniques, including conventional monoclonal antibody methodology e.g., the standard somatic cell hybridization technique of Kohler and Milstein. The preferred animal system for preparing hybridomas is the murine system. A monoclonal antibody according to the invention may be produced by a method comprising: immunising a non-human mammal with tRV conjugated to a hapten as an immunogen; obtaining an antibody preparation from said mammal; and deriving therefrom monoclonal antibodies that specifically recognise tRV. In one instance, the tRV described in the Examples of the present application may be employed to raise antibodies of the invention.

Polyclonal antibodies may be produced by routine methods such as immunisation of a suitable animal, with the antigen of interest. Blood may be subsequently removed from the animal polyclonal antisera obtained therefrom. Where polylonal antisera are raised for administration to subjects to treat or prevent pain according to the invention, immunisation is typically carried out on a non-human mammal or a bird, e.g. a horse, sheep, pig, goat, rabbit, cow, monkey, rat, mouse or chicken.

Antibodies of the invention can be purified by standard techniques known in the art, such as affinity chromatography.

The term "antigen-binding portion" of an antibody refers to one or more fragments of an antibody that retain the ability to specifically bind to tRV. It has been shown that the antigen-binding function of an antibody can be performed by fragments of a full-length antibody. Examples of binding fragments encompassed within the term "antigen-binding portion" of an antibody include a Fab fragment, a F(ab')$_2$ fragment, a Fab' fragment, a Fd fragment, a Fv fragment, a dAb fragment and an isolated complementarity determining region (CDR). Single chain antibodies such as scFv antibodies are also antibodies within the meaning of the invention. These antibody fragments may be obtained using conventional techniques known to those of skill in the art, and the fragments may be screened for utility in the same manner as intact antibodies.

Once a suitable monoclonal antibody has been identified and selected, the amino acid sequence of the antibody may be identified by methods known in the art. The genes encoding the antibody can be cloned, for example using degenerate primers. The monoclonal antibody can then be recombinantly produced by routine methods. The present invention also provides a cell line expressing an antibody of the invention. The cell line may, for instance, be a hybridoma, it may be cell line into which the nucleic acid sequences encoding the antibody of the invention are introduced.

In one instance of the invention, the antibody employed will be the antibody produced by the hybridoma 2H9. In another instance of the invention, the antibody employed will be the antibody produced from the 1B1 hybridoma.

The 2H9 hybridoma has been deposited by IP Science Ltd at the Russian National Collection of Industrial Microorganisms (VKPM) Depositary, FGUPGosNIIGenetika, Russia 117545, Moscow, 1 Dorozhny proezd 1 under Accession Number VKPM H-121 on 30 Aug. 2011. Similarly the 1B1 hybridoma has been deposited by IP Science Ltd at the Russian National Collection of Industrial Microorganisms (VKPM) Depositary under Accession Number VKPM H-122 on 30 Aug. 2011.

The present invention provides a hybridoma capable of producing the 2H9 antibody and a hybridoma capable of producing the 1B1 antibody. In particular, the present invention provides the VKPM H-121 and VKPM H-122 hybridomas, as well as equivalent hybridomas and derivative hybridomas of the VKPM H-121 and VKPM H-122. Such a derivative hybridoma will be capable of producing one of the antibodies as defined herein and preferably the 2H9 or 1B1 antibody.

The antibody employed in the invention may be one whose heavy and/or light chains have at least 70%, preferably at least 75%, more preferably at least 80% and even more preferably at least 85% sequence identity to those of the 2H9 or 181 antibody. In some instances, the level of sequence identity may be at least 85%, preferably at least 90%, more preferably 95% and still more preferably at least 96, 97, 98 or 99% sequence identity.

A variety of programs may be used to calculate percentage homology and sequence identity. The UWGCG Package provides the BESTFIT program which can be used to calculate homology (for example used on its default settings) (Devereux et al (1984) *Nucleic Acids Research* 12, p 387-395). The PILEUP and BLAST algorithms can be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al, supra). These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

In one instance, the antibody employed will have at least three, preferably at least four, more preferably at least five and still more preferably all six of the CDRs from the antibody 2H9. Alternatively the antibody may have that number of CDRs from the 1B1 antibody.

In a further instance, the antibody may have a CDR that has one of the above specified levels of sequence identity to one of the CDRs of either the 1B1 antibody or the 2H9 antibody. In one instance, the antibody employed may have at least three, preferably at least four, more preferably five such CDRs. In an especially preferred embodiment the antibody may have six CDRs which all have one of the above levels of sequence identity to the corresponding CDRs from the 1B1 antibody or the 2H9 antibody. In a further instance of the invention, the antibody employed may be one of the types of the types of antibody fragments referred to herein, which has the above-specified CDRs.

In one instance, the antibody employed has the framework regions from either the 1B1 antibody or the 2H9 antibody, or framework regions with one of the above-specified levels of sequence identity to the framework regions of the 1B1 antibody or 2H9 antibody. In a preferred instance, such framework regions are employed with the above-specified CDRs. In one instance, the entire heavy and/or light chain variable sequence from the 1B1 antibody or 2H9 antibody is employed. In another, the variable regions have one of the above specified levels of sequence identity to the variable region of the light and/or heavy chains of the 1B1 or 2H9 antibody.

In one instance, the antibody employed may have the entire sequence of the variable regions of the heavy and/or light chains of the 2H9 or 1B1 antibody, except for up to 50 amino acid substitutions, preferably up to 40 substitutions, more preferably only up to 30 such substitutions and even more preferably only up to 20 such substitutions. In one instance, the antibody has up to 15, preferably up to 10, more preferably up to 5 substitutions. The sequence may only have, in some instances, 4, 3, 2 or 1 such changes. In one instance, the number of amino acid changes may be in the range between any of the previously specified values. It may be the antibody may have from 1 to 10, 1 to 8, 1 to 6 or 1 to 4 amino acid changes. In some instances, the antibody will have such a number of sequence changes in their variable regions. In a preferred instances, the substitutions will be conservative.

Conservative substitutions may be made, for example according to the following Table. Amino acids in the same block in the second column and preferably in the same line in the third column may be substituted for each other.

| | | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

The antibodies employed will be able to bind tRV. In a preferred instance, the antibodies will be able to bind with at least the same affinity as the 1B1 or 2H9 antibody to tRV. In one instance, the antibody employed may display the ability to cross-block 1131 or 2H9 antibody binding to tRV. For instance, the antibody employed may bind the same epitope, or an overlapping epitope, as the 1B1 antibody or the 2H9 antibody.

Assays & Methods

The invention also provides for use of an antibody to detect tRV and in particular the antibodies described herein for such a use. In one instance, the invention also provides a method of detecting tRV, where the method comprises: (i) contacting a sample to be tested with an antibody against tRV; and (ii) detecting any binding of the antibody to tRV. The contacting of (i) being performed under conditions allowing the binding of the antibody to tRV. Such methods may be used to quantify tRV by determining the amount of binding of the antibody to tRV.

Any antibody based detection method may be employed. Hence, the invention provides an immunoassay for tRV. In one instance, the method of the invention may be any suitable antibody based assay, for example: a radioimmunoassay, a magnetic immunoassay, a fluorescent or luminescent immunoassay, a redox based assay or other electric current or electric signal generating detection assays.

In one particularly preferred instance of the invention the antibodies of the invention may be employed in an ELISA (Enzyme-linked immunosorbent assay). Hence, the invention provides an immunoassay for tRV and in particular an ELISA for tRV. ELISA is typically a heterogeneous, solid phase assay that requires the separation of reagents. The ELISA may, for instance, be an indirect ELISA. The ELISA may be a sandwich ELISA or a competitive ELISA. The ELISA may be a rapid ELISA.

The sandwich technique requires two antibodies against tRV. The first specifically binds tRV and is bound to a solid support. The binding of tRV by the first antibody may then be detected with a second antibody against tRV which recognises the tRV bound to the first antibody. The binding of the second antibody may be detected by any suitable means. For instance, the second antibody may be conjugated to an enzyme allowing its detection. Alternatively, the second antigen may be able to bind the enzyme, for instance because the antibody is biotinylated and the enzyme is conjugated with streptavidin. The antibody itself may be labelled. The second antibody may be recognised by a further antibody, allowing detecting through that binding, for instance because the third antibody is labelled or can bind to an enzyme. In such assays, the first and second antibody may be the same antibody against tRV or they may be different antibody against tRV.

The assay of the invention may be a competitive assay, for instance, a competitive ELISA. Labelled tRV may be added to compete with any unlabelled tRV present in the sample and hence reduction in binding of the labelled tRV to the antibody of the support allows the amount of unlabelled tRV to be quantified.

Any suitable solid surface may be used as a support in the assays of the invention. For instance, it may comprise, or consist essentially of, a polyvinylidene difluoride (PVDF) membrane. In some instances, the support of the invention may be selected from polystyrene, PVC, Perspex or Lucite. Typically, antibody immobilised on the support will be distributed evenly over the area it is present on. The surface may be the base of a well, such as a well of a microtitre plate. The plate may be suitable for automation of the assay. The support may, for instance, be a microtitre plate. The microtitre plate may, for instance, contain 24, 48 or 96 wells and in particular 96 wells.

Conditions suitable for coating the surface of the support with antibodies are well known in the art. Generally, an antibody may be bound to the surface by contacting the surface with the antibody under conditions suitable for antibody binding and washing to remove unbound antibodies. The surface may be "blocked" prior to addition of the cells. Suitable blocking agents are well known in the art and include bovine serum albumin (BSA), casein or fetal calf serum. The aim of blocking is typically to saturate the binding capacity of the surface in order to minimize binding of the secondary detection reagents and thereby preventing background. However, blocking is an optional step and in some instances, the method may not involve a blocking step.

Any suitable means of detecting binding of the antibody to the tRV may be employed. For instance, the antibody bound to tRV may be detected directly or indirectly. The antibody may be conjugated with a label. Suitable labels are well known in the art. The assays of the invention may, for instance, use a fluorogenic or luminogenic substrates for the enzyme conjugated to the antibody. In some instances, the antibody itself may be directly labelled with a fluorescent or luminescent molecule. The antibody may be labelled with, for example, an enzyme, a fluorochrome or a radioisotope, hence allowing detection of the antibody. Examples of enzymes that may be employed, for instance via conjugation to an antibody in the assays of the invention, include alkaline phosphatase and horseradish peroxidase. Examples of fluorochromes that may be employed include fluoroscein (particularly Oregon green) and rhodamine (particularly texas red). Where the antibody is biotinylated, a streptavidin conjugated moiety may be used to detect the antibody, for instance a streptavidin conjugated enzyme, including any of those mentioned above. The antibody may be detected using a further antibody.

In all detection steps, it is desirable to include an agent to minimise non-specific binding of the antigen. For example bovine serum albumin (BSA) or foetal calf serum (FCS) may be used to block non-specific binding.

The assays of the invention may comprise washing after particular steps, for instance after the immobilisation, after incubation with the test sample, after addition of a second antibody and so on. The assay of the invention may comprise: (i) contacting a sample to be tested with an antibody against tRV; and (ii) detecting any binding of the antibody to tRV. Step (i) may comprise an incubation step, which may be followed by a washing step.

Positive and negative controls may be performed with the assays of the invention. For instance, a positive control known to contain tRV may be employed. Samples with known amounts of tRV may be used to help quantify tRV via the assay of the invention. Such samples may be used to produce a standard curve. Negative controls which are known to lack tRV may also be used. Such controls may be provided with the kits of the invention. The kit of the invention may include a solution of tRV of known concentration to use as a standard.

The assays of the invention may be automated. For instance, the assays of the invention may include steps such as pipetting, incubation, washing, transferring microplates between activities, reading and data analysis and any, or indeed all, of such steps may be automated. Automation may, for instance, be used for any of sample distribution, dilution, incubation at specific temperatures, washing, enzyme conjugate addition, reagent addition, reaction stopping and the analysis of results.

The assay of the invention may be performed using a biochip, comprising an antibody of the invention.

The assays of the invention may be used to produce scales for tRV content.

The antibodies of the invention may also be used in the purification of tRV. The invention provides the use of the antibodies of the invention for such a purpose and also methods for purifying tRV comprising employing the antibody to recover and/or purify tRV. The methods may comprise contacting a solution containing tRV to the antibody allowing the antibodies to bind tRV, then recovering the bound tRV from the antibodies.

Samples for Analysis

The invention may be used to detect or measure tRV in any suitable sample. The invention may be used to measure tRV in an alcoholic drink, in particular in a wine. The wine may, for instance, be a red, white or rose wine and in particular is a red or rose wine, preferably a red wine. The assay may be used to measure tRV levels in a fortified wine or a spirit.

In one instance, the invention may be used to measure tRV in grapes. For instance, in a sample prepared from grapes, but which is yet to be fermented. The assays of the invention may also be employed to measure tRV levels in a fermentation broth. The invention may be use to compare tRV levels between two or more different samples of grapes, for instance from different vines, such as comparing tRV levels in two different varieties of grapes. The invention may also be employed in the production of vines that produce increased levels of tRV. For instance, by identifying vines to cross to produce strains which produce higher levels of tRV, or progeny which produce the highest levels of tRV. The invention may also be used to measure tRV levels over time, for instance to produce a time course for tRV production over time. Such measurement may be used to monitor tRV levels during the production of a food or beverage and also determine how the production can be altered to increase levels. The invention may be used to measure tRV in a food stuff or in a supplement.

In one case, the invention may be employed to measure tRV in a biological sample, particularly a biological sample from an animal, particularly a mammal and preferably a human. The assay may be use to measure tRV in blood, plasma or serum and in particular in serum. The sample may be urine. The invention may be used to determine how tRV levels vary in serum over time or between different individuals. The assays of the invention may be used to measure tRV after consumption of a tRV containing food, drink or food supplement, particularly after the consumption of a drink, preferably wine.

The invention may also be applied for the measurement of tRV in any of the following:
cocoa beans raw and processed, and their products, hard and liquid, such as cocoa powder, chocolate, and cacao drinks, in one preferred embodiment the invention is applied to a chocolate containing product, such as chocolate itself or a chocolate drink;
peanuts raw and cooked or processed, and their products, hard and liquid, such as peanut powder, butter and powder;
cranberry, blueberry, bilberry and other berries, as well as fruits and vegetable containing tRV, raw or processed, and their products, in a powder or liquid forms, in one instance the invention may be applied to measure tRV content in a fruit juice, fruit juice concentrate or fruit base drink, such as, for instance, a cranberry, blueberry or bilberry drink.

In one instance, the assay is performed on a sample prepared by ethyl acetate extraction, particularly where the assay is performed on serum. In one instance, the assay of the invention is performed on PBST plates. In another instance, the assay is performed using an assay employing the antibody against tRV conjugated with HRP, the means of detection may be tetramethylbenzidine combined with hydrogen peroxide, with, for instance, the reaction then being stopped with sulphuric acid.

In one instance, when the assay is performed on subjects, they may first have a "wash-out" period where the subjects avoid anything which might contain tRV. Where the assay being performed involves consuming a given sample thought to contain tRV, subjects may be asked to avoid other tRV containing food or drink for the duration of the assay.

Kits

The present invention also provides kits for performing the assays of the invention. Such kits will comprise an antibody of the invention. Where an antibody of the invention is used to detect tRV bound to an immobilised antibody of the invention, the antibody may be labelled as discussed herein or be able to bind a label as discussed herein.

The kits may also comprise a support for performing the assay of the invention and any of those discussed herein. In one instance, the kit may comprise a support with the antibody of the invention already immobilised on it or in some instances the two may be separate allowing the user to immobilise the antibody. A kit of the invention may also comprise a standard solution of tRV for use as a calibration or as a positive control.

EXAMPLES

Example 1

Obtaining of Immunogenic Conjugate of tRV with Bovine Serum Albumin

Results

To obtain conjugates of tRV with Bovine Serum Albumin, BSA, the following sequence of reactions was employed.

Acylation, or alkanoylation, or trans-Resveratrol ($^1$H-MNR spectrum of tRV in DMSO-$d_6$ is presented in FIG. 1). (1) by anhydride of succinic acid (2) under the heat in acetonitrile resulted in a mixture of hemisuccinate, or hemisuccinate-RV complexes (3a, 3b or 3c) and unmodified tRV. To monitor the reaction Thin Layer Chromatography was used on Kieselgel 60 $F_{254}$ plates. Detection of the reagent and their products was done either by using iodine vapours, or by using λ254 nm, Spectroline CX-20. The spot of the product (or its mixture) (3) in ethyl acetic acid-ethanol 96% mixture (4:1 oσ./oσ.) had $R_f$~0.53, tRV spot (1) had $R_f$~0.69.

The structure of the hemisuccinate-tRV (3) produced under these conditions was not studied, because it was not critical for further synthesis.

Activated N-oxysuccinimide ether (6) was produced after adding of N-hydroxysuccinimide (4) and N,N'-decyclohexilcarbodiamide (5) to an acid, or a mixture of acids, (3) in the reaction containing acetonitrile and 1,4-dioxane.

After separation of precipitated N,N'-dicyclohexylurea (7) a solution of hapten (6) in acetonitrile-dioxane mixture was introduced for interaction with BSA (AB, 8), diluted in 0.1 M solution of bicarbonate sodium.

The object of the synthesis—conjugate of RV-AB (9)—was purified by dialysis against 0.02 M of $NH_4HCO_3$ solution (in 2 L—2 times replacement) and against 0.01 M of $NH_4HCO_3$ (1 replacement) during 28÷29 hs.

The content of the dialysis sack was certificated at 16,000 r/min, Beckman J21 centrifuge (rotor G20), for 50 min. Supernatant was collected and gel-filtrated on the 40 cm column with 180 ml of Sephadex G15, balanced by 0.01 M solution of bicarbonate ammonia. Spectrophotometery at 278 nm was used for the product detection.

The fraction of the product (9), collected in 30 ml, was aliquoted in 3.5 ml in glass tubes, and frozen in liquid nitrogen, and the lyophilised on Crist® Alpha I-6 for 26÷27 hs. Altogether about 95 mg of the conjugate (9) was obtained.

Figure 3:
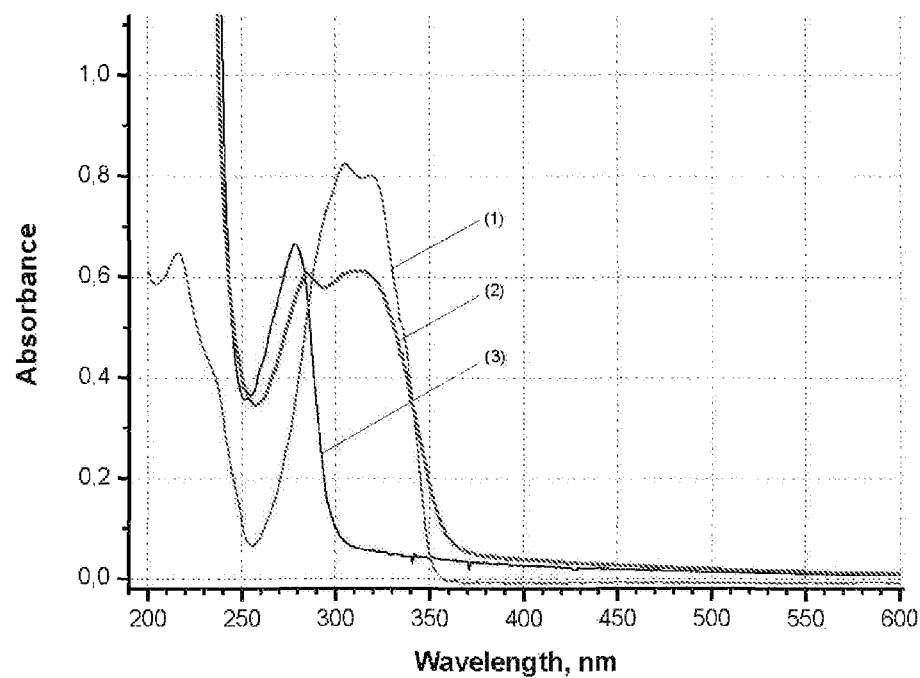
FIG. 3 shows absorption spectra of: 1—tRV in acetonitrile (0.0004 mg/ml); 2—RV-BSA conjugate (9) in water; and 3—BSA in water (1 mg/ml).

When 13-14 mg of the dried product (9), contained in a single tube, was mixed with 3 ml of distilled water about 90-95% of this product was fully diluted. After the dilution UV spectrum of the solution was 10 times repeatedly recorded by using Helios α. A comparison of the absorption spectra of the conjugate, free BSA and free tRV is presented in FIG. 3.

Example 2

Generation of Mouse Monoclonal Antibodies Against tRV

Immunisation

RV-BSA was diluted in the isotonic (physiological) saline at the concentration of 1 mg/ml. For immunisation female BALB/c mice were used with a body mass of 18-20 g. For each immunisation 2 groups of animals were used. Mice were immunised 3 times with intervals of 3 weeks between the first and second injection of the antigen, and 2 weeks between the second and third injection of RV-BSA.

For the first immunisation 100 mg of the antigen per mouse, with complete Freund's adjuvant, was injected intraperitoneally. For the second immunisation 200 mg of the antigen per mouse was used with incomplete Freund's adjuvant. For the third immunisation antigen dose was 100 mg with incomplete adjuvant. A booster dose of antigen, 200 mg per mouse, was injected intraperitoneally in 2 weeks after the third immunisation without the adjuvant.

Serum Antibody Production

From the time of the second immunisation sera from the mice was tested for the presence of specific antibodies by using ELISA Serum of the clinically healthy BALB/c mice, to which the antigen was not injected, was used as a negative control.

For this test 0.1 ml of antigen (RV-BSA, BSA, Ovalbumin, RV-Ovalbumin) at a concentration of 5 mg/ml in 0.1 M of carbonate buffer, pH9.5, was added into wells of microplates (Greiner®, Germany). Microplates were then incubated for 18 hours at +4° C. and washed four times with 0.01 M PSB with 0.1% Tween-20 (PBST). Control wells of the microplates were blocked by 1% Top Block (Yuro®, Switzerland) in PBS. The plates were then incubated for another 30 minutes at +37° C., the blocking solution removed, and then 0.1 ml serum from mice #1 and #2 was added in different dilutions in PBST (from 1:1000 to 1:128000) with 0.5% of BSA.

The microplates were then incubated for 1 hour at +37° C., and then HRP conjugated antibodies against mouse IgG (Sigmma®, USA) were added in their working dilution. The plates were then incubated for a further one hour at +37° C. Unbound reagents were washed out by BSAT. Trimethylbenzene, TMB, was used as a chromogenic substrate for HRP. The intensity of the colour development, after stopping the reaction by 1M $H_2SO_4$, was measured by spectrophotometer Multiscan EX (Thermo®, USA) at λ450 nm.

Figure 4:
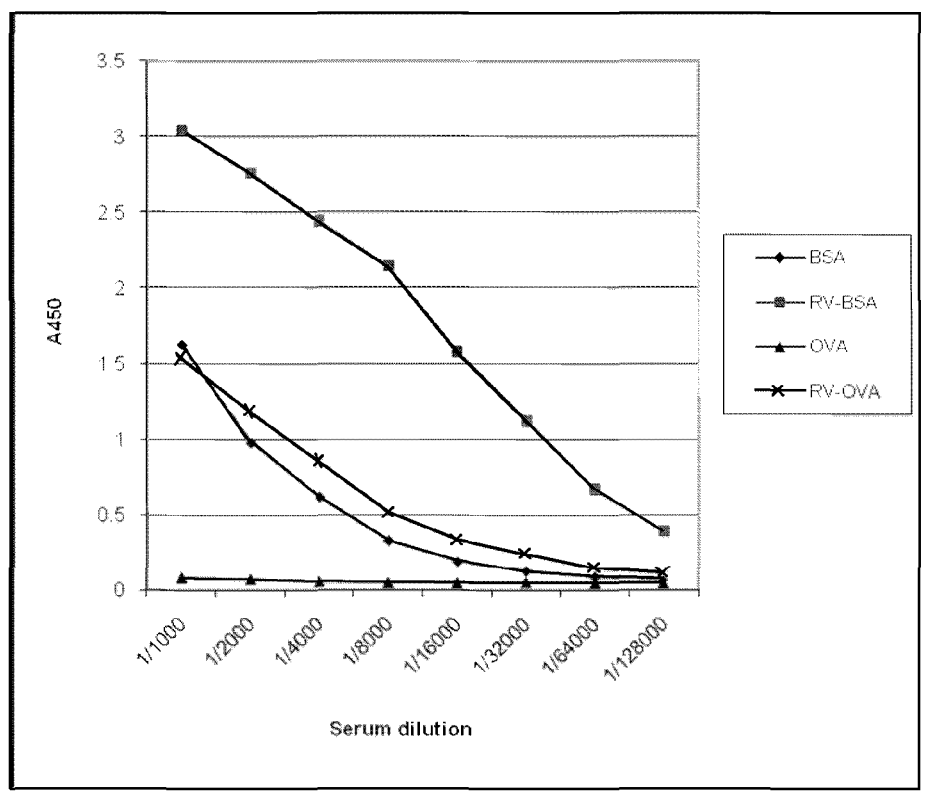
FIG. 4 shows titres of the serum from mouse #1, RV-BSA (the antigen used for immunisation); OVA—Ovalbumin, RV-OVA—conjugate of tRV with OVA.
Figure 5:
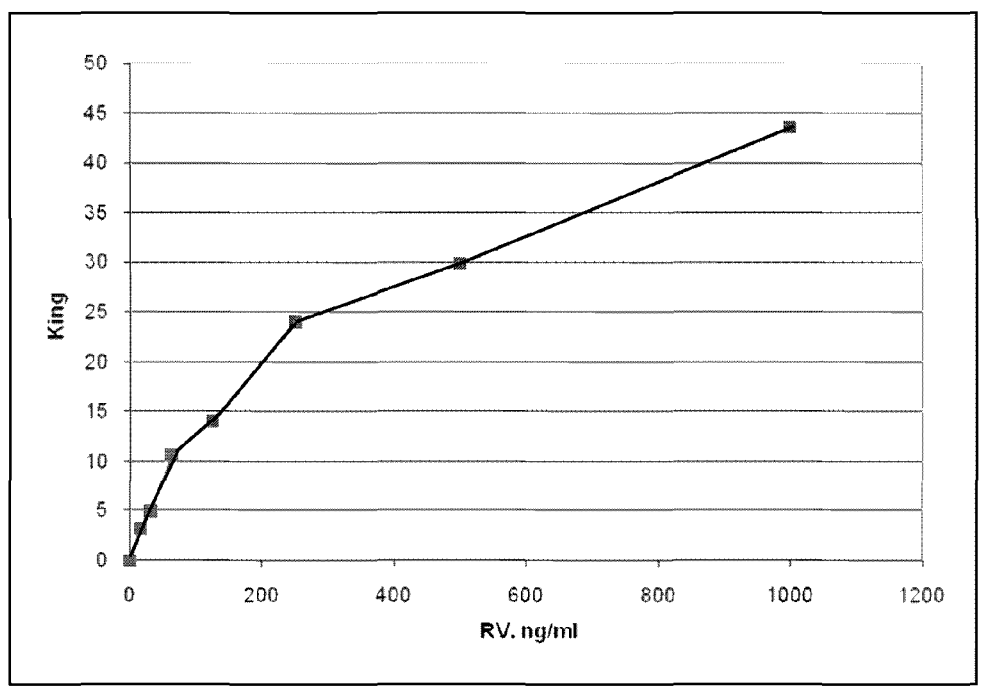
FIG. 5 shows the results of competitive analysis to measure antibodies against tRV in serum from mouse #1.

The results of titration of the immune serum after the third immunisation of mouse #1 are presented on the FIG. 4.

These results illustrate that the strongest immune response was against conjugated Resveratrol (RV-BSA), with BSA itself the response was weaker. Serum antibodies did not react with pure Ovalbumin but did with the RV-Ovalbumin conjugate. That indicates that the serum possibly interacts with two components of the latter—Resveratrol itself and/or the linking part of the conjugate which binds Resveratrol and the protein.

Antibody Specificity—Further Assessment

To confirm the generation of antibodies against tRV, the serum was tested on the ability of free tRV to inhibit the binding of the serum to RV-OVA immobilised in the wells of the microplates. In the absence of free tRV, specific serum antibodies should only bind Resveratrol in immobilised RV-OVA, and after adding of anti-mouse HRP conjugates, the signal should be maximal. When free tRV is present, part of the specific antibodies should able to interact with it. This in turn leads to reduction of the level of the antibodies available for the binding with the immobilised Resveratrol, RV-OVA complexes. Therefore, in this case the HRP signal would be reduced.

A solution of 5 μg/ml of RV-OVA in 0.1M carbonate buffer pH=9.5, was added into microplate wells and left there overnight. After 4 times washing out and blocking wells with 1% Top Block in PBS, free tRV was added in 50 μl in each well in the dilutions from 15 ng/ml to 1000 ng/ml. (The stock solution contained 1 mg/ml of tRV, 0.5% of BSA and 10% of ethanol). 50 μl of sera from mice #1 and #2 were added after their dilution to 1/1000 by BSAT, containing 0.5% of the albumin. The content of the wells was mixed using a shaker for one minute, and then plates were incubated for one hour at +37° C.

The microplates were washed out four times with BSAT and the HRP conjugate against mouse IgG was added in its working dilution. Samples were then incubated for one hour at +37° C. TMB was used as the substrate for HRP. The intensity of the colour development, after stopping the reaction by 1M $H_2SO_4$, was measured by spectrophotometer Multiscan EX (Thermo®, USA) at λ450 nm.

The ability of free tRV to inhibit the binding of antibodies to the immobilised conjugated Resveratrol ($K_{in}$) was calculated as follows:

$$K_{in}=100-[A_{450}tRV/A_{450}C]\times100$$

$A_{450}tRV$—absorption of samples containing free tRV
$A_{450}C$—absorption of the Control sample without free tRV The results obtained are presented in FIG. 4 and confirm that the tested serum contains IgG class antibodies that are able to specifically interact with free tRV. A similar analysis was performed with the serum from mouse #2. It was shown that although the serum was interacting with RV-OVA, the addition of free tRV did not affect binding of the antibodies with the immobilised conjugate. In other words, this serum did not contain antibodies specific against free tRV (data not shown) and hence mouse #2 was not used for further work.

Hybridomas 767 hybridoma cell lines were produced from mouse #1. From the ninth day of growing hybridoma cell cultures, the hybridomas were tested for their ability to produce specific anti-tRV antibodies. The indirect ELISA, which was used for the testing serum described above, was employed to test the hybridomas. RV-BSA was used as the specific immobilised antigen, BSA as the control.

Figure 6:
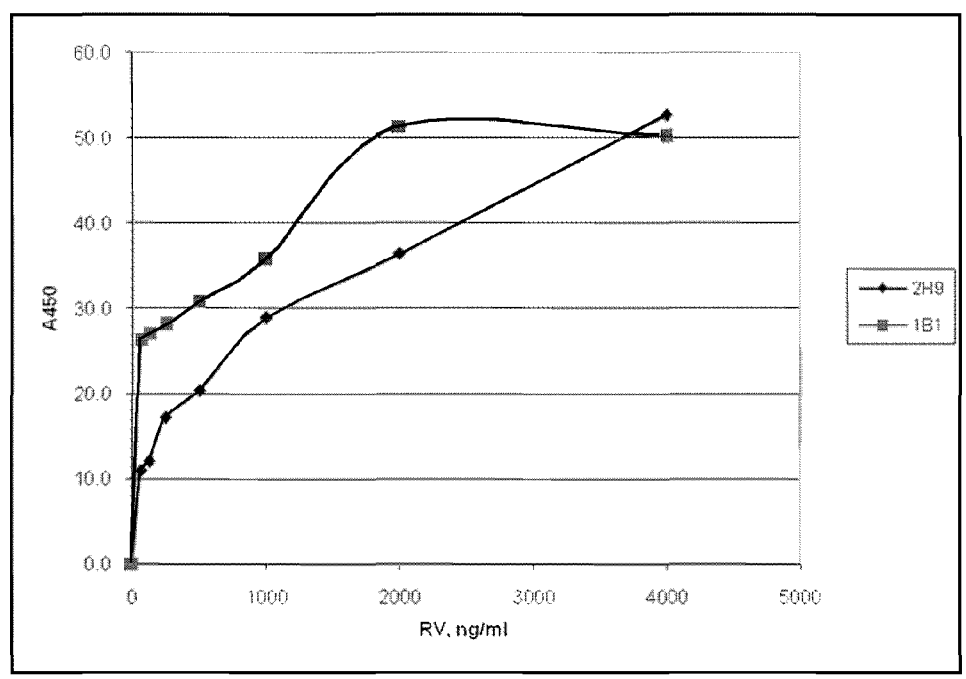
FIG. 6 shows the results of competitive analysis for tRV by using monoclonal antibodies from hybridomas 2H9 and 1B1.

From screening the hybridoma cell lines generated only 16 clones were obtained which were able to interact with RV-BSA, but not with BSA itself. From those clones, eight clones were stable enough to maintain their antibody production in 24-well plates. Antibodies specific for free tRV from all eight of the lines were tested. Only two hybridomas, 2H9 and 1B1, were found to produce IgGs specific for free tRV. The results for those two hybridomas are presented in FIG. 6. Antibodies from the other six hybridomas were inactive in the test (data not shown). Antibodies from the two positive hybridomas can be used in the assays of the invention.

Example 3

Measurement of tRV in Wine

The same indirect ELISA assay described above used to measure tRV in serum was applied to measure the concentration of tRV in selected wine samples.

For example, tRV concentration in red wine of La Fleur de Bouard 2004, La Lande de Pomerol was 2,800 ng/ml (12.2 µM), ($K_{in}$-36.7), and in another red Joseph Drouhin 2005, Beaune-Champimonts was 4,300 ng/ml (18.8 µM) ($K_{ing}$=53.0). The summary of the results obtained are presented in Table 2.

Example 4

Measurement of Resveratrol in the Serum

Resveratrol Extraction from the Serum 2 ml of ethyl acetate was added to 0.5 ml of serum sample, then mixed on a vortex for 3 minutes, followed by centrifugation for 2 minutes at 500 r/min. The upper layer of ethyl acetate was transferred into a new tube. To the remaining lower water fraction a second portion of 2 ml ethyl acetate was added and the extraction procedure was repeated. The new ethyl acetate fraction was added to the old one, giving a total volume of 4 ml, which was then dried by air flow at 60° C., using a Reacti-Therm™III, Thermo scientific, USA.hyyh. 40 µl of ethanol was then added and mixed on vortex, then 160 µl of PBS with 0.5% BSA was added and mixed again. This final solution was used for the analysis described below.

Immunoenzyme Assay for Measurement of Resveratrol

RV-BSA was pre-absorbed on microplate wells in 0.1M carbonate buffer, pH=9.5 (at a concentration of 5 µg/ml) overnight at 4° C. After washing four times the PBST plate was blocked with PBS contacting 1% of Top Block (<<Yuro>>, Switzerland).

For the calibrating curve different concentrations of tRV were added into the wells. The stock solution used was 1 mg/ml of tRV diluted in PBST with 0.5% BSA and 20% ethanol. 50 µl of each serum extract to be tested were added to parallel wells. After which 50 µl of the conjugate of HRP with monoclonal anti-tRV antibodies was added to all the wells. The content of the wells was mixed using a shaker for 1 minute and then the plate was then incubated for 1 hour at +37° C.

The plate was washed out four times with PBST, and then a chromogeninc substrate was added, tetramethylbenzidine+ $H_2O_2$. After stopping the reaction with 1M $H_2SO_4$, optic density was read at λ450 nm, Multiscan EX (<<Thermo>>, USA).

Inhibition by free tRV of the binding of serum antibodies with immobolised RV-BSA ($K_{in}$) was calculated according to the following formula:

$$K_{in}=100-(A_{450}D/A_{450}C-)\times 100,$$

where:

$A_{450}D$ is the optic density in samples with free tRV (testing serum or samples from the calibrating curve), $A_{450}$ C is the an optic density without free tRV.

Figure 7:
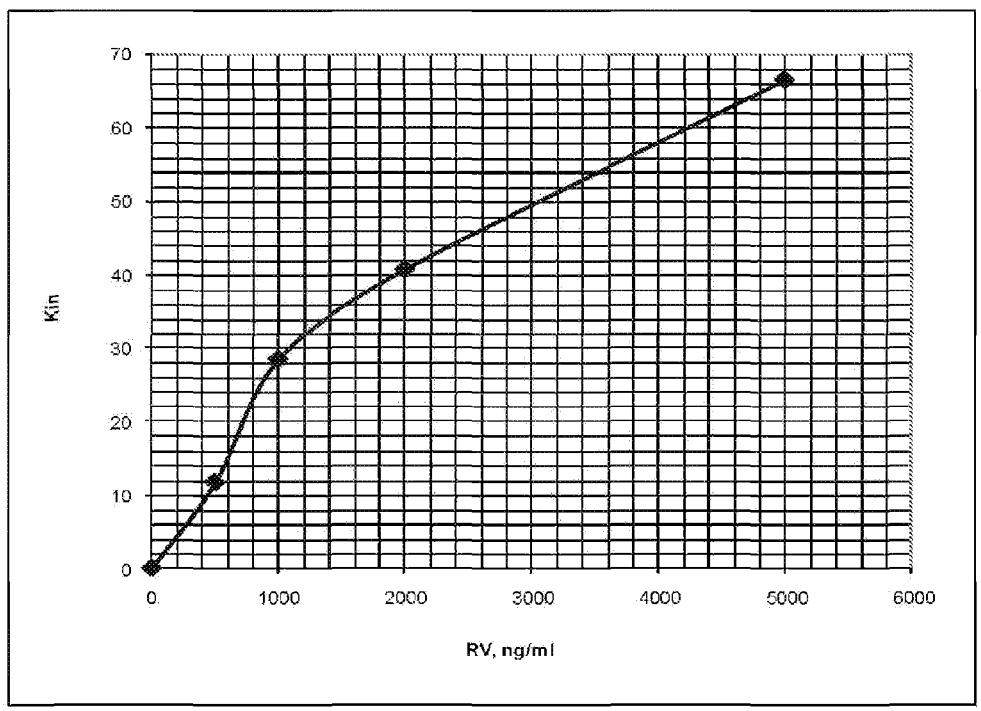
FIG. 7 shows dependence of $K_{in}$ from tRV concentration in calibrating curve samples.

The Concentration of tRV was determined using the calibration curve shown in FIG. 7.

Example 5

Cross-Over Study of Comparative Bio-Availability of tRV from its Different Nutraceutical Formulation and Different Wines Nutraceutical Study The group of 5 volunteers comprised of 2 female and 3 male clinically healthy Caucasian persons, age between 23 and 35 years.

They were asked, before commencing this experiment, to go for 3-4 days "wash-out", when consumption of any grape, wine, peanut, chocolate and other products which might contain them.

In the morning of the experiment, one hour after light breakfast, volunteers were given 1 gelatine capsule containing 100 mg of tRV.

Blood samples were taken from their median cubital or cephalic veins at the baseline point. Then, after administration of tRV, their blood was taken again at the following time points: 30 minutes, 1 hour, 2, 3, 4, 6 and 8 hours. After 4 hours time point volunteers had a light lunch which did not involve consumption of any grape, wine, peanut, chocolate and other products which might contain them.

After taking blood its serum was separated, aliquoted and stored at −80° C. for further testing.

Wine Study

The same volunteers also participated in a wine study. The same "wash out" period was used, and the same timing of the experiment was applied. Instead of taking a capsule of tRV each of the volunteers consumed 200 ml of red wine, which was selected on a basis that it would contain 1 mg of tRV in this volume. The rest of the Protocol employed was the same as above.

After taking blood, serum was separated, aliquoted and stored at −80° C. for further testing. The results obtained are shown in Table 1a below.

TABLE 1a

Comparison of HPLC-MS and anti-tRV ELISA methods to measure tRV in human serum: after administration of 100 mg of tRV as a dietary supplement.

| | Concentration of tRV in serum, in ng/ml as a sum of 7 separate measurements after administration of tRV: 30 min + 1 h + 2 h + 3 h + 4 h + 6 h + 8 h | |
|---|---|---|
| Volunteers | HPLC-MS | ELISA |
| 1 | 98 | 1600 |
| 2 | 139 | 1900 |
| 3 | 79 | 1070 |
| 4 | 37 | 795 |
| 5 | 107 | 1412 |

TABLE 1b

Comparison of HPLC-MS and anti-tRV ELISA methods to measure tRV in human serum: after administration of 1 mg of tRV in 200 ml of red wine.

| | Concentration of tRV in serum, in ng/ml as a sum of 5 separate measurements after administration of tRV: 1 h + 2 h + 4 h + 6 h + 8 h | |
|---|---|---|
| Volunteers | HPLC-MS | ELISA |
| 1 | 6 | 310 |
| 2 | 572 | 850 |
| 3 | 0 | 120 |
| 4 | 0 | 460 |
| 5 | 0 | 380 |

TABLE 2

Comparison of HPLC-MS and anti-tRV ELISA methods to measure tRV in wine.

| | Concentration of tRV in wine, in ng/ml | |
|---|---|---|
| Wine | HPLC-MS | ELISA |
| Boudreaux red | 3.6 ± 0.7 µg/ml | 2.8 ± 0.5 µg/ml |
| Burgundy red | 5.7 ± 0.9 µg/ml | 4.3 ± 1.1 µg/ml |
| California red | 1.5 ± 0.3 µg/ml | 1.2 ± 0.5 µg/ml |
| California white | 0.2 ± 0.4 µg/ml | 0.4 ± 0.3 µg/ml |
| English white | 0.1 ± 0.3 µg/ml | 0.1 ± 0.2 µg/ml |

TABLE 3

Comparison of HPLC-MS and anti-tRV ELISA methods to measure pharmacokinetics of tRV in human serum: after administration of 100 mg of tRV as a dietary supplement.

| | Time after administration of 100 mg of | Concentration of tRV in serum, in ng/ml | |
|---|---|---|---|
| Volunteers | tRV | HPLC-MS | ELISA |
| 1 | 30 min | 8 | 140 |
| | 1 h | 65 | 650 |
| | 2 h | 12 | 210 |
| | 3 h | 11 | 20 |
| | 4 h | 0 | 135 |
| | 6 h | 2 | 420 |
| | 8 h | 10 | 25 |
| 2 | 30 min | 0 | 90 |
| | 1 h | 97 | 490 |
| | 2 h | 21 | 255 |
| | 3 h | 0 | 10 |
| | 4 h | 9 | 195 |
| | 6 h | 12 | 620 |
| | 8 h | 0 | 240 |

Example 6

Additional Information

The following provides some additional information on the materials and methodology employed in the preceding Examples and also some further comments on the results seen.

Materials

Trans-Resveratrol (t-RSV) was obtained from Kaden Biochemicals GMBH, Germany (#621309). Bovine serum albumin was purchased from Amresco Inc, Solon, Ohio, USA (#332). Ovalbumin (OV) and Freund's adjuvant were from Sigma Aldrich, St. Louis, Mo., USA (# A5503 and F5881). ELISA plates were purchased from Greiner Bio-One, Germany (#762070). Liquid Substrate System for ELISA reagents was obtained from Sigma Aldrich, St. Louis, Mo., USA (#10440). Female BALB/c mice aged 3 months were ordered from Puschino Breeding Facility (Moscow, Russia).

All other chemicals, solvents and supplies were purchased from Sigma Aldrich (St. Louis, Mo., USA) unless specifically mentioned otherwise. All aqueous solutions including HPLC buffers were prepared using Millipore Milli Q grade water. Wine varieties were purchased from a general grocery supplier in Cambridge, UK.

Antigen Generation

All glassware was oven- or flame-dried for 10 hours and cooled in a nitrogen atmosphere. Antigen preparation required chemical modification of t-RSV which was performed according to a modified protocol of Y. L. Jiang et al (2008) *Bioorg Med Chem.* 16(12): 6406-14.

Hapten Synthesis

Figure 8:
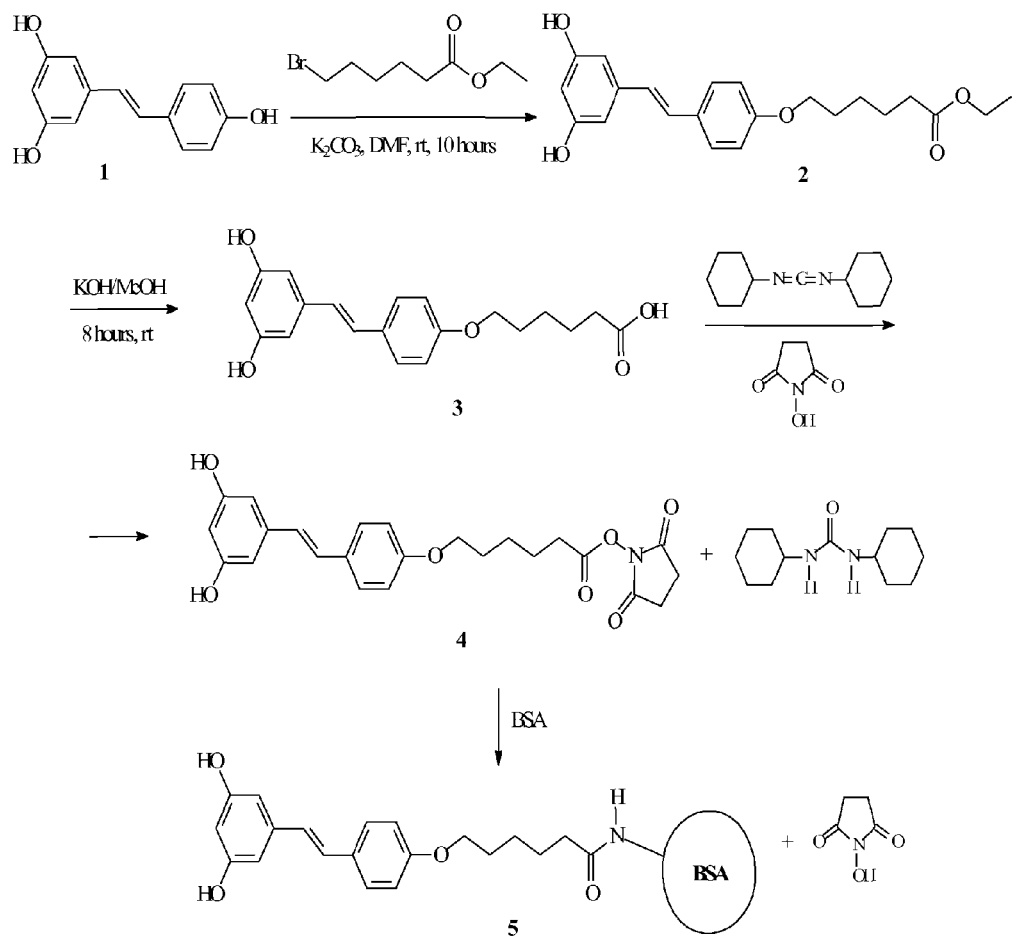
FIG. 8 shows the t-RSV hapten synthesis scheme referred to in Example 6.
Figure 9A:
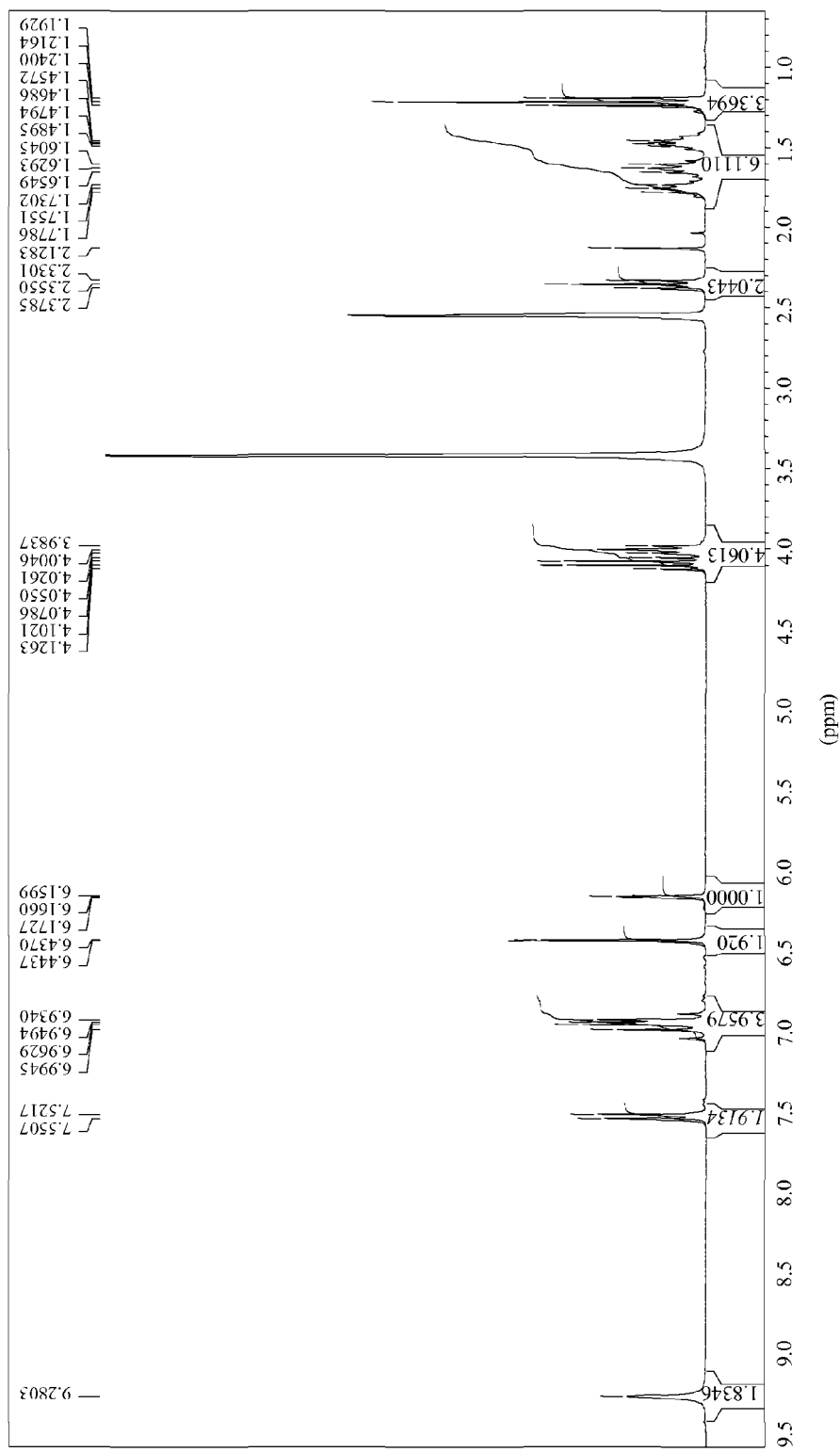
FIG. 9 shows the $^1$H NMR spectra of ester 2 (A) and acid 3 (B) in CDCl$_3$ referred to in Example 6.
Figure 9B:
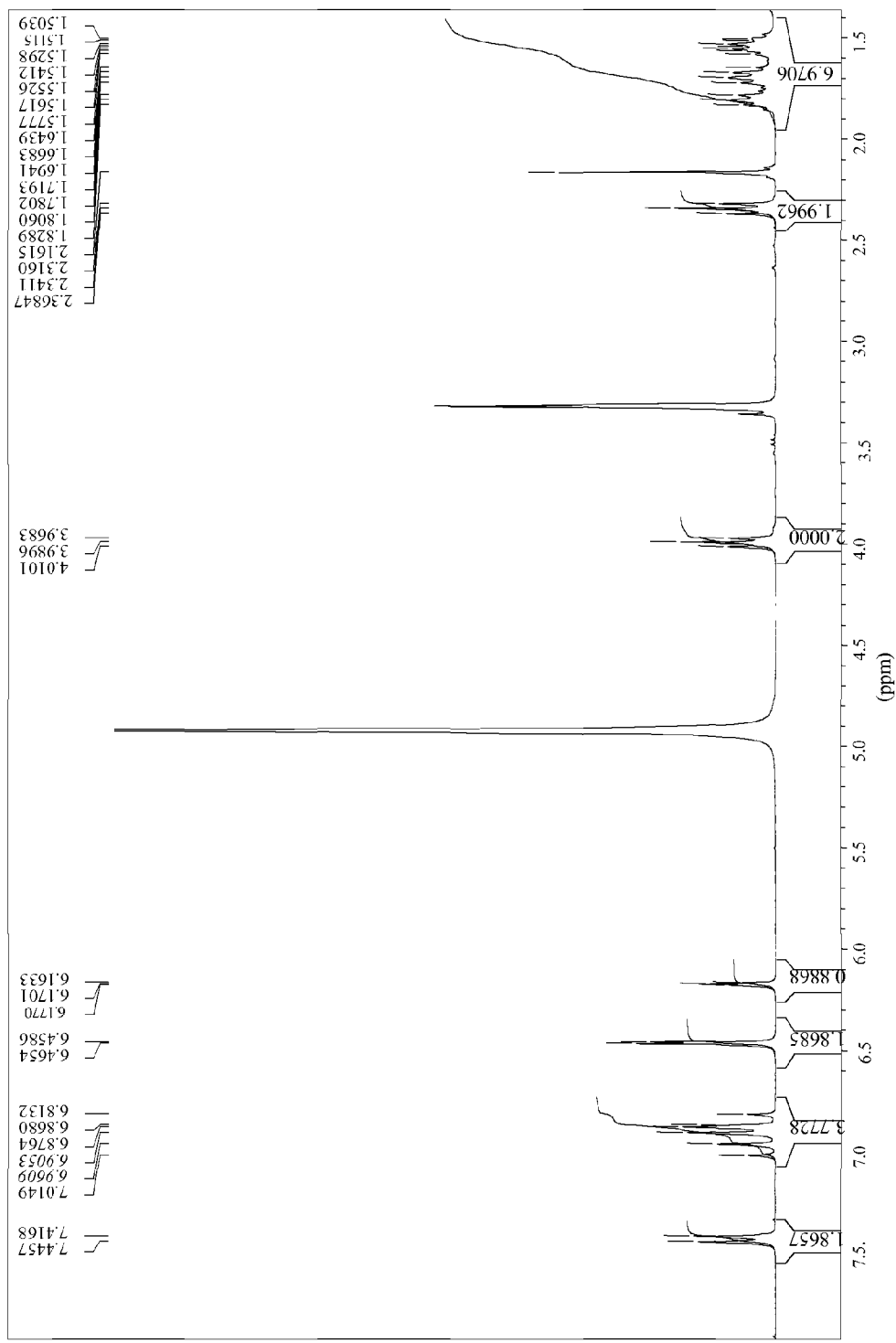
Figure 10:
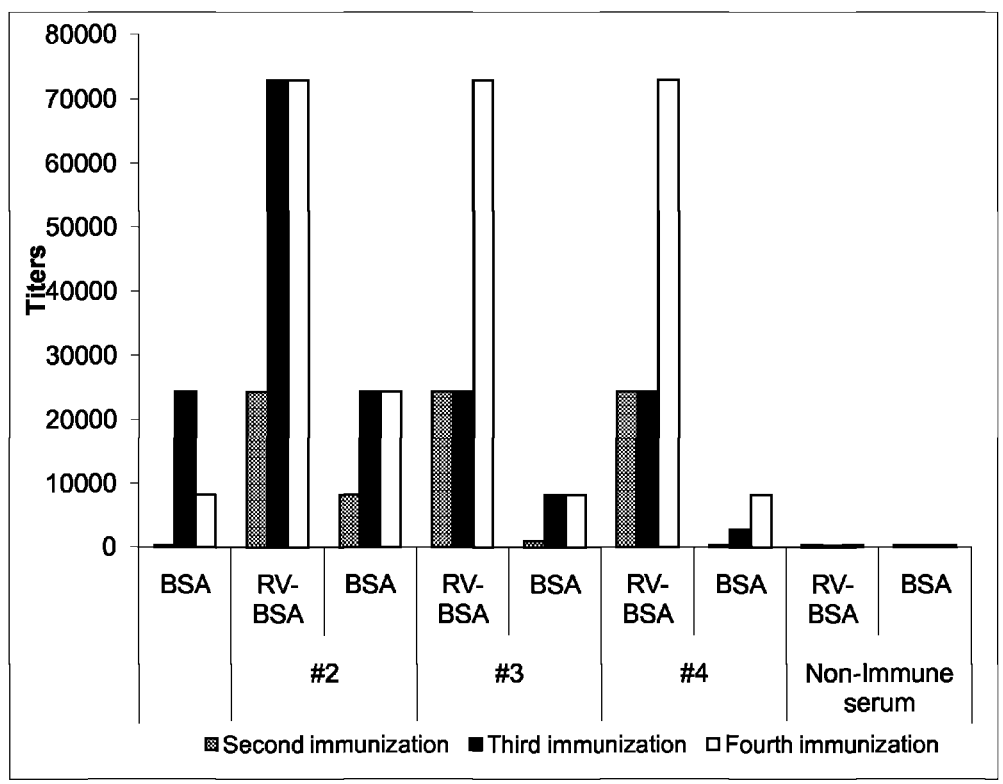
FIG. 10 shows immune response in Balb/c mice injected with t-RSV-BSA conjugate discussed in Example 6.

Briefly, the introduction of a carboxyl group into the t-RSV structure required for the preparation of a t-RSV-OV and t-RSV-BSA conjugates was performed by selective O-alkylation of the hydroxyl group at the 4'-position with ethyl-6-bromohexanoate. The resulting derivate[2] was isolated and fully characterized by NMR analysis (FIG. 8). Next, a saponification of derivate 2 was accomplished with potassium hydroxide solution in methanol to obtain free acid 3, which was used for coupling with carrier proteins (BSA and OV). The identity of derivates was confirmed with NMR on a Bruker AV-300 spectrometer (FIGS. 9 and 10). Brief protocols for hapten generation and the t-RSV-coupling procedure are presented below.

O-Alkylation. $K_2CO_3$ (1.33 g, 9.64 mmol, 1.1 equiv) and ethyl-6-bromohexanoane (2.93 g, 13.14 mmol, 1.5 equiv) were added under argon to a solution of resveratrol[1] (2.00 g, 8.76 mmol) in DMF (10 mL). After stirring overnight, the mixture was diluted in EtOAc (100 mL) and washed with 1

N HCl (3×50 mL). The organic layer was dried over MgSO$_4$ and filtered. The solvent was evaporated under reduced pressure and the residue was purified by flash chromatography using CH$_2$Cl$_2$/EtOAc 10:1.5 as eluent to afford 0.4 g of 2 (30%). Rf value, 0.71 (acetone/hexane, 50:50, v/v). Mp 182-183° C. $^1$H NMR (DMSO-d$_6$, ppm) δ 1.21 (t, 3H, J=7.4 Hz, CH$_3$); 1.47 (m, 2H, CH$_2$), 1.63 (m, 2H, CH$_2$); 1.77 (m, 2H, CH$_2$); 2.35 (t, 3H, J=7.2 Hz, CH$_3$), 4.00 (t, 2H, J=6.4 Hz, CH$_2$), 4.09 (k, 2H, J=7.4 Hz, OCH$_2$); 6.16 (t, 1H, J=2.2 Hz, Ar—H), 6.42 (d, 2H, J=2.2 Hz, Ar—H), 6.92 (m, 4H, Ar—H), 7.56 (d, 2H, J=8.4 Hz, Ar—H), 9.28 (s, 2H, OH).

Saponification. Compound 2 (0.2 g) was dissolved in a 5% solution of KOH in methanol (10 ml). The resulting mixture was stirred for 12 hours at room temperature. The mixture was extracted with ethyl acetate twice (2×10 mL) to remove starting material and then the water phase was acidified to pH 2 using 6 N HCl and extracted with ethyl acetate (2×10 mL) again. The organic phase was evaporated on a rotary evaporator, the residue was purified with column chromatography on silica gel using a mixed solvent (acetone/petroleum ether with a gradient of 1:2-1:1) to give compound 5 (0.142 g, 62%). R$_f$ value, 0.82 (HOAc/EtOAc=5/95). Mp 196-197° C. $^1$H NMR (CD$_3$OD, ppm) δ 1.52 (m, 2H, CH$_2$); 1.65 (m, 2H, CH$_2$); 1.75 (m, 2H, CH$_2$); 2.34 (t, 3H, J=7.2 Hz, CH$_3$), 3.98 (t, 2H, J=6.2 Hz, CH$_2$), 6.17 (t, 1H, J=2.2 Hz, Ar—H), 6.45 (d, 2H, J=2.2 Hz, Ar—H), 6.91 (m, 3H, Ar—H), 6.94 (d, 2H, J=16.1 Hz, Ar—H), 7.43 (d, 2H, J=8.8 Hz, Ar—H). Active ester 4 was synthesized by the treatment of free acid 3 (100 mg) with dicyclocarbodiimide (DCC, 78 mg) and N-hydroxysuccinimide (80 mg) in 1.5 ml of DMF at room temperature. The precipitate (dicyclohexyl urea) was filtered out and the mother solution was used for the conjugate synthesis.

Conjugation

The final conjugate 5 was obtained by adding compound 4 (100 mg) in dimethylformamide to an aqueous solution (0.1 M NaHCO$_3$) of bovine serum albumin (250 mg) with further incubation of the resulting mixture (t-RSV-BSA) at 4° C. for 10 hours. In the same manner the second conjugate was prepared starting from 100 mg of 3 and 250 mg of ovalbumin (t-RSV-OV). Conjugation products were dialyzed for 28 hours against 0.02 M NH$_4$HCO$_3$ with a further switch to 0.01 M NH$_4$HCO$_3$. Dialyzed solutions were centrifuged at 10.000 g and passed through a Sephadex G15 column balanced with 0.01 M NH$_4$HCO$_3$. Final products were lyophilized and kept under nitrogen. The efficiency of conjugation was measured and the resulting t-RSV conjugates were characterized using fluorescent spectroscopy as described by others (Soukpoe-Kossi (2006) j Biomol Struct Dyn. 24(3): 277-83). It was assumed from the beginning and confirmed once an ELISA had been developed that t-RSV conjugates are stable for at least one month when stored at −20° C.

Standard Solutions

A stock solution of t-RSV was made in 50% methanol and water and kept in small aliquots at −80° C. in darkness. The frozen solution was thawed by 1 hour exposure to room temperature. Unused portions of aliquots were discarded. Working solutions of t-RSV were made by dissolving in PBST supplemented with 10% ethanol. For the ELISA protocol 0.5% BSA was added to the working solutions. ELISA calibration specimens were made by spiking PBST-ethanol with increasing amounts of t-RSV within 2 hours of the scheduled assay.

Antibody Generation

All animal procedures were approved by the local Animal Research Ethical Committee at Moscow Institute of Virology. Solutions of t-RSV conjugates (t-RSV-OV and t-RSV-BSA) for animal use were prepared in 0.9% NaCl on the day of injection. Mice were immunized three times with a 3 week interval between the first and second injections of conjugates and a 2 week interval between the second and third injection of t-RSV conjugates. The first immunization was performed by intraperitoneal injection of 100 μg of t-RSV-BSA or t-RSV-OV conjugate with complete Freund's adjuvant (1:1 vol/vol). The second immunization was done subcutaneously by injection of 200 μg of t-RSV conjugate with Freund's incomplete adjuvant. 100 μg of t-RSV conjugates with Freund's incomplete adjuvant were used for the third immunization. Immunized mice were boosted intraperitoneally with 200 μg of t-RSV conjugates with no adjuvant added 2 weeks after the third immunization.

Sera Evaluation

Serum specimens obtained from the immunized mice were routinely screened using indirect ELISA starting from the second round of immunization.

Titer Check

Greiner Bio-One 96-well ELISA microplates (Germany) were coated at room temperature for 2 h and at 4° C. overnight, with 100 μL t-RSV-BSA, t-RSV-OV or BSA and OV alone (5 μg/ml in 0.1 M carbonate buffer, pH 9.5). Plates were washed 3 times with PBST. Control sera from non-immunized mice and sera from immunized mice were diluted with PBST supplemented with 1 mg/ml BSA. 100 μl serial dilutions ranging from 1:1000 to 1:128000 were pipetted into the wells of the ELISA plates with further incubation of the plates at 37° C. for 1 hour. After three washings with PBST, addition of goat peroxidase-labeled antibody against mouse IgG was made. Further incubation of the plates at 37° C. for 1 hour was followed by three PBST washes and addition of 100 μl/well of tetramethylbenzidine (TMB) chromogenic substrate. After 30 min incubation at room temperature, the color reaction was stopped by adding 50 μl/well 1 N H$_2$SO$_4$, The plates were read at 450 nm (Multiscan EX, Thermo Scientific, Waltham, Mass., USA). The titers were measured for each individual mouse after every immunization.

Hybridoma Construction 72 hours after the final intravenous boost, the spleens of anesthetized mice (positive responders) were removed and dispersed and the resulting splenocytes were fused with Sp-2 cells and incubated in HAT medium according to the conventional protocol (Maniatis et al (1998) Molecular Cloning: A Laboratory Manual. Cold Spring Harbor Pr5ess, Cold Spring Harbor, N.Y.). Positive wells were inspected microscopically for cluster formation and the supernatants were tested for antibody presence by indirect ELISA. Positive clones were subcloned by limiting dilution protocol using spleen feeders. Antibodies were isotyped with a mouse monoclonal antibody isotyping reagent.

Specificity Evaluation

An indirect competitive ELISA assay was used to evaluate the specificity of immune response in the mice as well as immunoglobulins produced by hybridoma clones. ELISA plates were coated with each t-RSV conjugate or each carrier protein as described above. Serial dilutions of the competitor ranging from 15 ng/ml to 1000 ng/ml were made from a stock solution of t-RSV (1 mg/ml) in PBST supplemented with 0.5% BSA and 10% ethanol. 100 μl of the competitor serial dilution and an aliquot of immune serum were inoculated into each well of the microplate. The amount of sera introduced into the wells was constant and corresponded to the serum dilution that produced an OD$_{450}$ reading ~1.0 as determined by the preliminary titer evaluation. The competitor and primary antibody were co-incubated for 1 hour at 37° C. with occasional gentle shaking of the plate. The further processing of the plates included washing and addition of TMB as described above. A competition assay for each serum specimen was done in duplicate. The readings were used to calculate inhibition value ($C_{Inh}$) according to:

$$C_{Inh}=100-[(A_{450+T\text{-}RSV}/A_{450\text{-}T\text{-}RSV})\times 100];$$

where $A_{450+T\text{-}RSV}$ is an optical density at 450 nm in the wells with t-RSV added versus the well with no addition of t-RSV ($A_{450\text{-}T\text{-}RSV}$). Similar format of indirect competitive ELISA was used for the evaluation of IgG produced by hybridoma clones.

Standard Curve Generation t-RSV-BSA or t-RSV-OVA were used as coating agents for an indirect competitive ELISA as described above in Specificity Evaluation. Serum specimens obtained from immunized mice were used as a source of primary antibody. Increasing concentrations of non-conjugated t-RSV mixed with aliquots of sera were preincubated on ice for 1 hour before inoculation into the wells of the ELISA microplate. All ELISA reactions for standard curve generation were performed in duplicate and were repeated three times. The mean values for the calibration curve within the linear range were fitted using linear regression analysis.

Further Results

Using the protocols described above we were able to conduct hapten synthesis according to the scheme shown in FIG. 8 and confirm the identity of the intermediates (ester 2 and acid 3) from $^1$H NMR spectra in $CDCl_3$. Free acid 3 was used for a coupling procedure with carrier proteins. The resulting conjugates were used for the immunization protocol. Injections of t-RSV conjugates into BALB/c mice produced a detectable immune response from the second round of immunizations. All mice injected with t-RSV-BSA had measurable antibody in serum to the immunogen (FIG. 8), while only 3 out of 7 mice injected with t-RSV-OV had some antibody response to the conjugate (results not shown). Over several attempts t-RSV-BSA was a better inducer of the immune response than t-RSV-OV. Moreover, FIG. 8 shows that all immune serum specimens obtained from the mice immunized with t-RSV-BSA demonstrated better recognition of the conjugate than BSA alone. This may indicate that immunization with t-RSV-BSA resulted in the production of antibody against t-RSV and the linkage zone of the conjugate allowing partial recognition of BSA.

The recognition pattern of BSA versus t-RSV-BSA by immune serum obtained from mouse #1 is presented in the FIG. 10. It reveals that recognition of t-RSV-BSA is much stronger than BSA alone.

Competition analysis confirmed the specific nature of antibody binding to t-RSV. Preincubation of immune serum with free t-RSV depleted significantly binding of antibody to t-RSV-BSA conjugate. Similar analysis was done with the serum specimens obtained from two mice immunized with t-RSV-OVA. In both cases addition of free t-RSV did not affect binding of the antibodies with the immobilized conjugate (results not shown). In other words, the serum specimens from the mice immunized with t-RSV-OVA did not contain antibodies specific to free t-RSV. Therefore our attempts to use t-RSV-OVA in the immunization protocol were terminated.

Splenocytes obtained from mouse #1 injected with t-RSV-BSA were used for the hybridoma construction. 767 primary hybridoma clones were established and tested by indirect ELISA with t-RSV-BSA and BSA alone. Expansion of the clones and their subsequent screening narrowed our work to 16 independent clones which were capable of recognition of t-RSV-BSA with little or no cross-reactivity to BSA alone. Further expansion of the clones limited our selection to eight cell lines which were stable enough to maintain antibody production. Finally, the cloning protocol employed allowed us to narrow our work to two IgG1a-producing hybridomas designated as 2H9 and 1B1.

The newly generated mAbs were used further tested in an indirect ELISA assay where mAb 2H9 displayed particularly good consistency and reproducibility on multiple occasions. mAb 2H9 had a little or no cross reactivity to cis-RSV. No recognition of trans-RSV-3-O-glucuronide and trans-RSV-3-sulfate was detected.

Additional Discussion of Results

The majority of analytical methods developed for measurement of low-molecular weight food constituents are based on extremely sophisticated instrumental techniques such as gas chromatography and high pressure liquid chromatography coupled with mass spectroscopy. These methods represent a supposed "gold standard" for many analytical protocols, including RSV analytical assays. Besides the need for expensive equipment and reagents, these methods are time-consuming and require highly skilled support personnel as well as specialized laboratory space.

In the present paper we report a successful hapten synthesis, preparation of a hapten-protein conjugate and generation of monoclonal antibody against t-RSV, a polyphenolic compound originating in grapes and berries. The newly generated mAbs can be used for the development of a novel immunoassay/s which can be employed for the detection of t-RSV in different biological and agricultural specimens. t-RSV-BSA conjugate gave the best performance in the immunization protocol while t-RSV-OVA complex was less immunogenic. The generation of mAb to t-RSV has never been reported before.

The invention claimed is:

1. A method of detecting or measuring trans-Resveratrol (tRV) in a sample, comprising:
   (i) contacting a sample to be tested with a monoclonal antibody against tRV; and
   (ii) detecting or measuring any tRV bound by the antibody, wherein the antibody of (i) is obtained from the hybridoma deposited under Accession Number VKPM H-121 or the hybridoma deposited under VKPM H-122.

2. The method of claim 1, where:
   (a) the antibody of (i) is bound to a support; and/or
   (b) the binding of tRV to the antibody of (i) is detected with a second antibody against tRV.

3. The method of claim 1, where the method is an ELISA method or a method performed using an antibody based chip or sensor.

4. The method of claim 1, wherein the sample to be tested is an agricultural, pharmaceutical, nutraceutical or cosmetic sample or is a biological sample from a human.

5. The method of claim 4, wherein the biological sample is human serum.

6. The method of claim 1, wherein the method provides a measurement for trans-Resveratrol defined by reference to a standard scale, chart, score for trans-Resveratrol.

7. A monoclonal antibody against tRV, where the antibody is obtained from the hybridoma deposited under Accession Number VKPM H-121 or the hybridoma deposited under VKPM H-122.

8. A hybridoma selected from the hybridoma deposited under Accession Number VKPM H-121 and the hybridoma deposited under Accession Number VKPM H-122.

9. A kit for detecting or measuring trans-Resveratrol (tRV), where the kit comprises the antibody of claim 7.

10. The kit of claim 9, wherein the kit also comprises:
(a) a support for immobilising the antibody to;
(b) a standard for tRV; and/or
(c) further antibody for detection of the antibody of claim 7; and/or
(d) instructions for performing the assay.

11. The kit of claim 9, wherein the antibody is labeled or biotinylated.

* * * * *